(12) United States Patent
Di Falco (10) Patent No.: US 9,664,817 B1
(45) Date of Patent: May 30, 2017

(54) FLEXIBLE METAMATERIALS OF VISIBLE WAVELENGTHS

(75) Inventor: Andrea Di Falco, Fife (GB)

(73) Assignee: UNIVERSITY COURT OF THE UNIVERSITY OF ST ANDREWS, St Andrews (GB)

(*) Notice: Subject to any disclaimer, the term of this patent is extended or adjusted under 35 U.S.C. 154(b) by 341 days.

(21) Appl. No.: 13/605,184

(22) Filed: Sep. 6, 2012

Related U.S. Application Data (60) Provisional application No. 61/532,461, filed on Sep. 8, 2011.

(51) Int. Cl.
*G02B 1/00* (2006.01)
*G02C 7/02* (2006.01)
*G02C 7/04* (2006.01)
*A61F 2/16* (2006.01)

(52) U.S. Cl.
CPC ............ *G02B 1/002* (2013.01); *A61F 2/1613* (2013.01); *G02B 1/007* (2013.01); *G02C 7/022* (2013.01); *G02C 7/049* (2013.01)

(58) Field of Classification Search
CPC .......... B82Y 5/00; B82Y 30/00; B82Y 35/00; B82Y 40/00; B82Y 99/00; G02C 7/04; G02C 7/041–7/049; A61F 2/16; A61F 2/1602; A61F 2/1613; G02B 1/00; G02B 1/002; G02B 1/005; G02B 1/007
USPC .................. 351/159.02–159.38; 623/4.1–6.62
See application file for complete search history.

(56) References Cited

U.S. PATENT DOCUMENTS

| | | | |
|---|---|---|---|
| 2008/0165442 A1 | 7/2008 | Cai et al. | |
| 2008/0296710 A1 | 12/2008 | Tonucci | |
| 2009/0040132 A1 | 2/2009 | Sridhar et al. | |
| 2009/0047745 A1 | 2/2009 | Magnera et al. | |
| 2009/0118605 A1* | 5/2009 | Van Duyne ........ A61B 5/14532 600/365 |
| 2010/0053030 A1* | 3/2010 | Sprague ............................. 345/7 |
| 2010/0053763 A1 | 3/2010 | Chowdhury et al. | |
| 2010/0066638 A1 | 3/2010 | Margomenos et al. | |
| 2010/0086750 A1 | 4/2010 | Blumberg et al. | |
| 2010/0108916 A1 | 5/2010 | Barker et al. | |
| 2010/0157437 A1* | 6/2010 | Higginson et al. ........... 359/652 |
| 2010/0271692 A1 | 10/2010 | Hor et al. | |

(Continued)

FOREIGN PATENT DOCUMENTS

| | | |
|---|---|---|
| CN | 101759374 | 6/2010 |
| WO | WO2005/089176 | 9/2005 |
| WO | WO2010/027753 | 3/2010 |

OTHER PUBLICATIONS

Rapp et al., "Regression methods for ophthalmic glucose sensing using metamaterials", Journal of Electrical and Computer Engineering—Special issue on Electrical and Computer Technology for Effective Diabetes Management and Treatment archive vol. 2011, Jan. 2011 Article No. 5.*

(Continued)

*Primary Examiner* — Darryl J Collins
*Assistant Examiner* — Gary O'Neill
(74) *Attorney, Agent, or Firm* — Moore & Van Allen PLLC; W. Kevin Ransom (57) ABSTRACT

A contact lens or visual prosthesis that includes at least one array or distribution of optical elements on a flexible substrate, the optical elements in the array or distribution being separated by or having a periodicity of less than 1 micron and each element having a dimension of 1 micron or less.

21 Claims, 6 Drawing Sheets

(56) References Cited

U.S. PATENT DOCUMENTS

| | | | |
|---|---|---|---|
| 2010/0278481 A1 | 11/2010 | Smolyaninov et al. | |
| 2010/0307553 A1* | 12/2010 | Defries | B82Y 20/00 136/243 |
| 2011/0069377 A1* | 3/2011 | Wu | G02B 1/007 359/356 |

OTHER PUBLICATIONS

Vladimir M. Shalaev, McCoy Lecture: Transforming Light with Metamaterials: A New Paradigm for the Science of Light, Feb. 15, 2010, published by Electrical and Computer Engineering, Purdue University, West Lafayette, IN , at http://nanohub.org/resources/8062/about.*

Xu et al., Flexible Visible-Infrared Metamaterials and their applications in Highly Sensitive Chemical and Biological Sensing, Jun. 22, 2011, ACS Publications, Nano Letters, pp. 3232-3238.*

Litchinitser et al: "Optical Metamaterials: Invisibility in Visible and Nonlinears in Reverse"; http://adsabs.harvard.edu/abs/2009npsm.book..217L.

Enkrich et al.: "Magnetic Metamaterials at Telecommunication and Visible Frequencies"; Physical Review Letters, vol. 95, No. 20 (2005), pp. 1-4.

Leonhardt: "Optical Conformal Mapping"; Science, vol. 312, Jun. 23, 2006, pp. 1777-1780.

Pendry et al.: "Controlling Electromagnetic Fields"; Science, vol. 312, Jun. 23, 2006, pp. 1780-1782.

* cited by examiner

FLEXIBLE METAMATERIALS OF VISIBLE WAVELENGTHS

CLAIM OF PRIORITY UNDER 35 U.S.C. §119

This Non-provisional Patent Application claims priority to U.S. Provisional Application Ser. No. 61/532,461, filed Sep. 8, 2011, entitled "Flexible Metamaterials of Visible Wavelengths," assigned to the assignee hereof and hereby expressly incorporated by reference herein.

FIELD OF THE INVENTION

The present invention relates to flexible metamaterials that operate in the visible range. In addition, the invention relates to the use of such metamaterials in contact lenses.

BACKGROUND OF THE INVENTION

Metamaterials are artificial materials that allow light to be to controlled and manipulated with precision. Metamaterials are materials that include periodic or non-periodic distributions of meta-atoms. They inherit their properties from the structures of the meta-atoms, rather than from the materials of which they are made. Typically, metamaterials are made by periodic arrangements of metallic nanofeatures, but more recently they have been realized with all-dielectric materials.

Metamaterials are "effective media", because the meta-atoms are typically smaller than the wavelength at which they operate. Thus, the media can be effectively considered homogeneous. Importantly, metamaterials allow the effective permittivity and permeability, and so the refractive index, to be specified locally, with high spatial accuracy.

Metamaterials have been known for some time. Examples of metamaterials that are effective in the visible range are described by Enkrich et al in "Magnetic Metamaterials at Telecommunication and Visible Frequencies" PHYSICAL REVIEW LETTERS PRL 95, 203901 (2005), the contents of which are incorporated herein by reference. Other examples of metamaterials are described by Ulf Leonhardt, et al in "Optical Conformal Mapping" Science 312, 1777 (2006), and by Pendry et al in "Controlling Electromagnetic Fields" Science 312, 1780 (2006)), the contents of both of which are incorporated herein by reference.

SUMMARY OF THE INVENTION

According to one aspect of the invention, there is provided a contact lens or visual prosthesis that includes an array or distribution of optical elements on a flexible substrate, the optical elements in the array being separated by or having a periodicity of less than 1 micron and/or each element having a maximum size of 1 micron in at least one dimension.

The separation or periodicity of the elements may be in the range 50 nm to 750 nm. The maximum dimension of each element may be in the range 50 nm to 750 nm.

The array or distribution may be periodic. The optical elements may all be the same. Alternatively, the array or distribution may comprise sub-arrays. Optical elements of different sub-arrays may be different.

The array or distribution of optical elements on a flexible substrate may comprise a flexible metamaterial.

Each optical element may be a resonant device, for example a nano-antenna or a split ring.

The flexible metamaterial can be embedded in the contact lens or prosthesis via several fabrication procedures. For example, the flexible metamaterial can be fabricated independently and then applied/incorporated to the contact lens/prosthesis. Alternatively, the metamaterial can be incorporated in or on the lens directly. The meta-atoms can be placed on the surface (external or internal) of the lens and/or embedded in the lens or prosthesis itself.

According to another aspect of the invention, there is provided a flexible metamaterial that is effective in the visible light range, e.g. 400 nm to 750 nm. By effective in the visible range, it is meant that the metamaterial is seen by visible light as being homogeneous, and is able to control and/or manipulate light in the visible range. For example, the metamaterial may be arranged to cause focusing or filtering of visible light.

The optical elements in the array or distribution are separated by less than the maximum wavelength of operation in the visible range, i.e. less than 750 nm, and each element has a maximum dimension of less than the maximum wavelength of operation, i.e. typically less than 750 nm.

In some embodiments, the optical elements are separated by or have a periodicity of less than half the maximum wavelength of operation in the visible range, and each element has a maximum dimension of half the maximum wavelength of operation

BRIEF DESCRIPTION OF THE DRAWINGS

Various aspects of the invention will now be described by way of example only and with reference to the accompanying drawings, of which.

DETAILED DESCRIPTION OF THE DRAWINGS

Figure 1A:
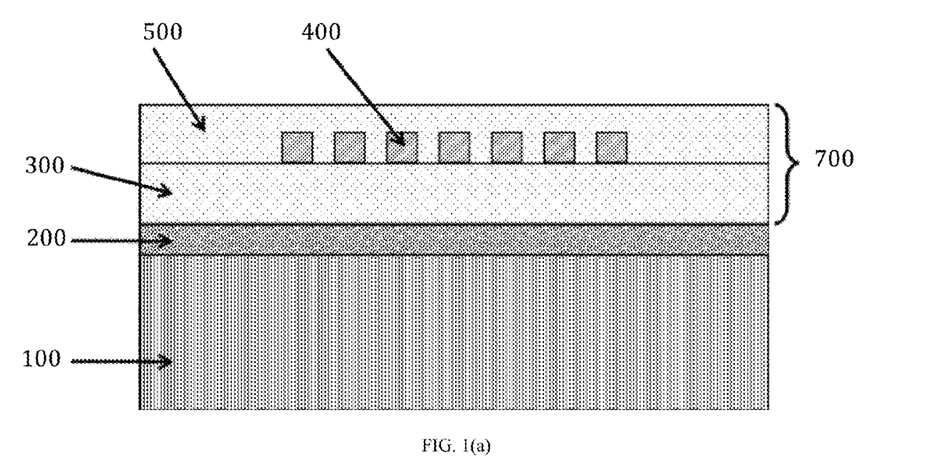
FIG. 1(a) is a cross section through an intermediate device in a process for making a flexible metamaterial that is effective in the visible range.
Figure 1B:
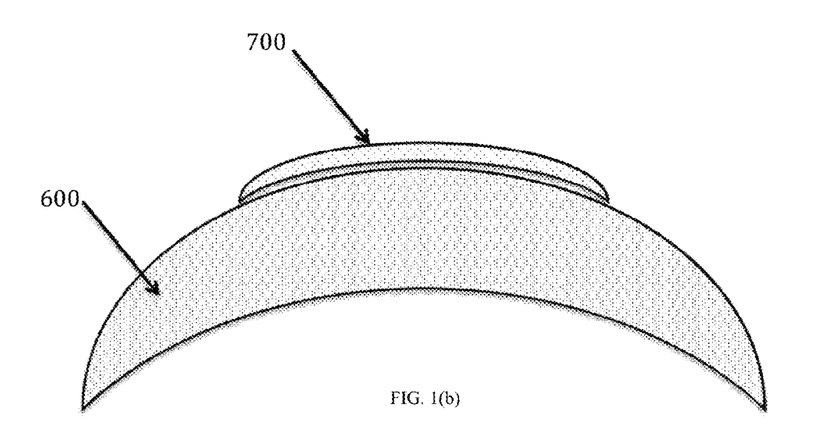
FIG. 1(b) is a cross section through a contact lens to which a flexible metamaterial has been applied.

FIG. 1 illustrates a method for making of a flexible metamaterial that is effective in the visible range. A planar substrate 100, for example made of glass, silicon, plastic or any other material suitable to the application, is coated with a release sacrificial layer 200. The sacrificial layer can be deposited e.g. via spin coating, spray or dip coating, drop casting, sputtering, evaporation, epitaxial growth or any other suitable technique. The sacrificial layer can be made of any polymer, semiconductor or any other material that can be subsequently dissolved/removed without affecting the other components of the final device. The thickness of the sacrificial layer is defined by the application, but can be as thin as 1-10 nm. A polymer 300, for example SU8, PMMA, polymide, or any other polymer that provides a required level of flexibility and optical transparency is then deposited on the sample via standard techniques. Typical thicknesses are from 1-10 nm to several mm. The polymer may be biocompatible.

Once the polymer layer is formed, the meta-atoms 400 are defined. The meta-atoms can be made of metal, e.g. silver, gold, aluminum, copper, etc. or other materials like ITO, ZnO, graphene or in other dielectric materials, like polymers or glass. The meta-atoms are of dimensions comparable with the wavelength of light in the visible range, with a minimum dimension in the range of 1-100 nm and maximum dimension less than or around 1 µm, and preferably less than 750 nm.

The meta-atoms are arranged in periodic or random fashion, with typical intra-atom distance smaller or larger than the operation wavelength. The nano-patterns can be fabricated using standard techniques, including photolithography, electron beam lithography, nano-imprinting, transfer printing, ink printing, nano-moulding or any combination of these. An additional coating layer 500 may be deposited on the pattern, with thickness from 1-10 nm to several mm, depending on the application. The coating layer can be made of different material, including metal or a polymer.

Using the same techniques, meta-atom patterns can also be stacked on top of each other to realize three-dimensional geometries. The stacking can be done by iterating the last two steps (pattern definition and coating layer). Alignment between two successive layers can be precise (for example less than 1 nm accuracy) or completely random. The properties of the alignment are dependent on the desired optical properties, and chosen according to the requirements of the application.

To release the membrane hosting the meta-atoms from the substrate, the sacrificial layer is dissolved via immersion in a suitable solvent (e.g. water, Acetone, acids, etc. . . . ), in optimized concentration and for the required amount of time. The released membrane can be placed on a contact lens 600 and incorporated onto it via chemical or thermal methods.

Figure 2:
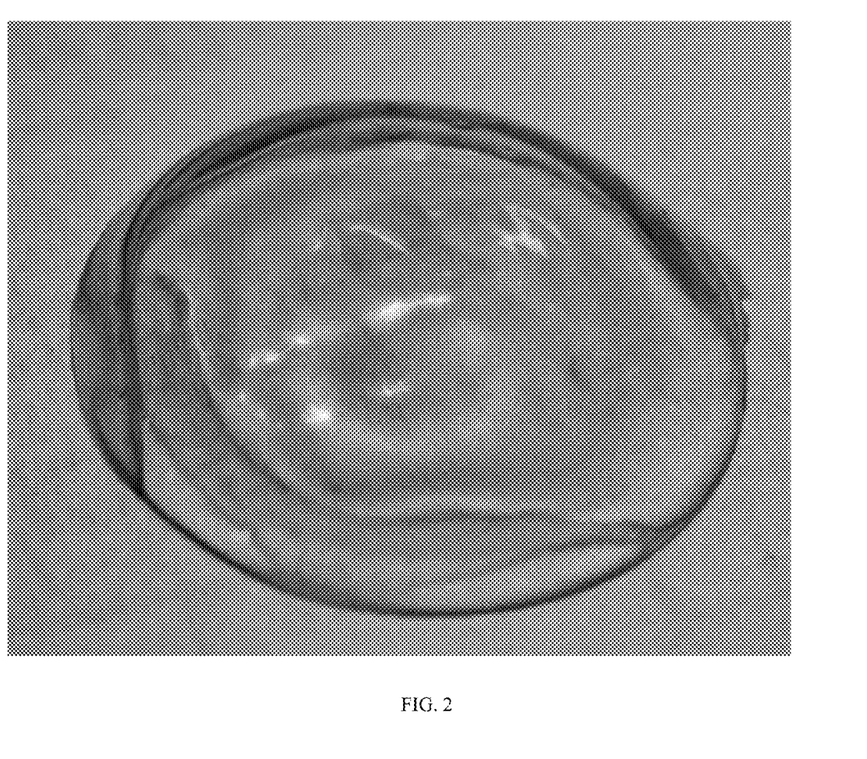
FIG. 2 is a photograph of a contact lens to which a flexible metamaterial is applied.

FIG. 2 shows a flexible metamaterial placed on (not bonded to) a disposable contact lens. Alternatively, the membrane could be used in combination with traditional molding techniques used to fabricate contact lenses.

Figure 3:
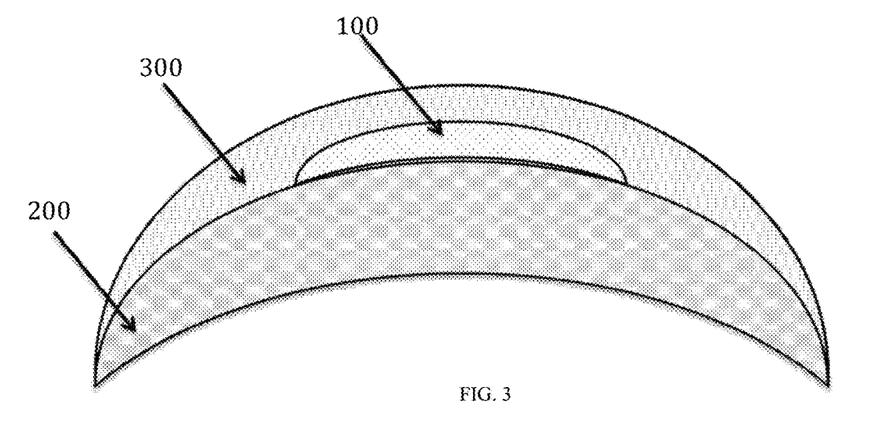
FIG. 3 is a cross section through a contact lens that includes a flexible metamaterial.

FIG. 3 shows an alternative fabrication method. The metamaterial layer 100 is directly imprinted/transferred onto an already shaped contact lens 200. The metamaterial can then be coated with suitable materials 300 or left exposed.

Figure 4A:
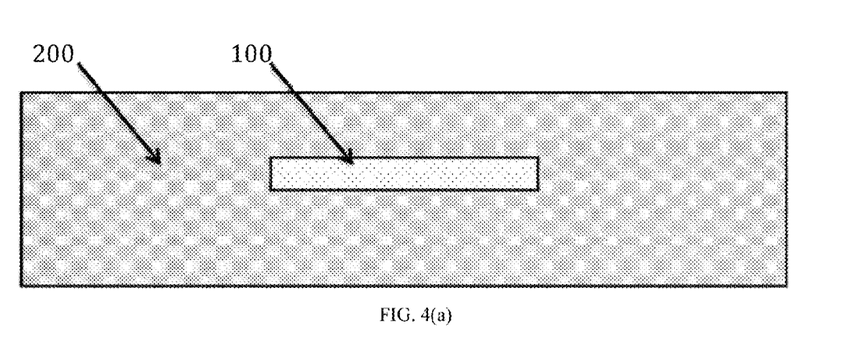
FIG. 4 is a cross section through another contact lens that includes a flexible metamaterial.
Figure 4B:
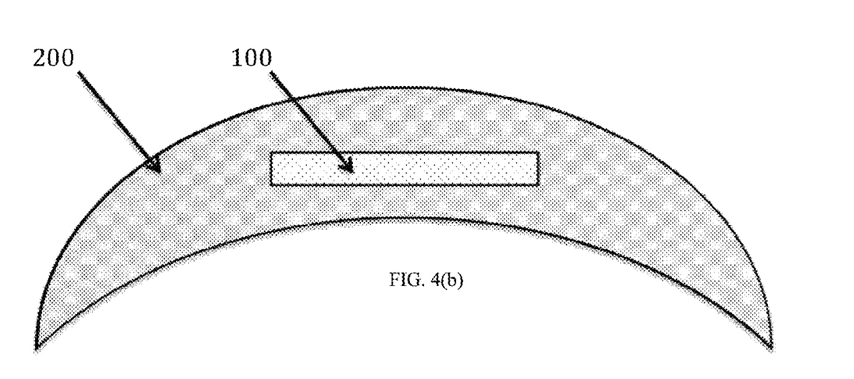

FIG. 4 shows an alternative fabrication method. FIG. 4(a): the previous procedure can be developed to the point where a planar arrangement (2D) or a 3D stack of meta-atoms 100 is embedded in a flat geometry into a suitable polymer 200. The optical prostheses will then be obtained with cutting procedures typical of contact lens, with mechanical or optical methods, as shown in FIG. 4(b).

Figure 5A:
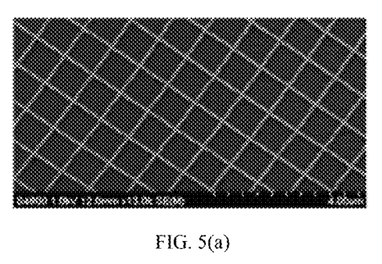
FIG. 5(a) is a front view of a "fishnet" metamaterial.
Figure 5B:
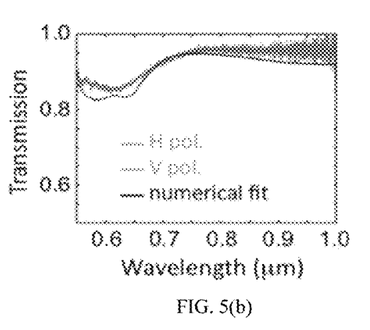
FIG. 5(b) is a transmission spectrum for the fishnet metamaterial of FIG. 5(a)
Figure 6A:
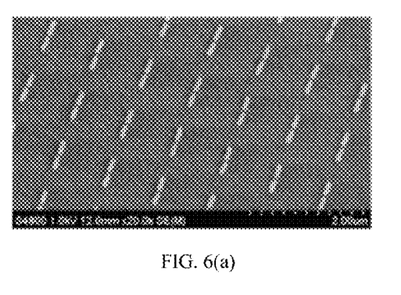
FIG. 6(a) is a front view of a micro-antenna based metamaterial.
Figure 6B:
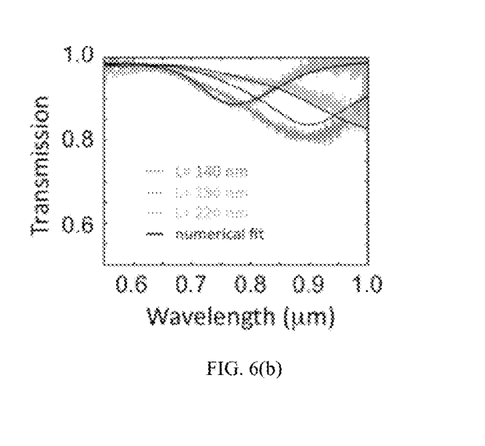
FIG. 6(b) is a transmission spectrum for the micro-antenna metamaterial of FIG. 6(a)
Figure 7A:
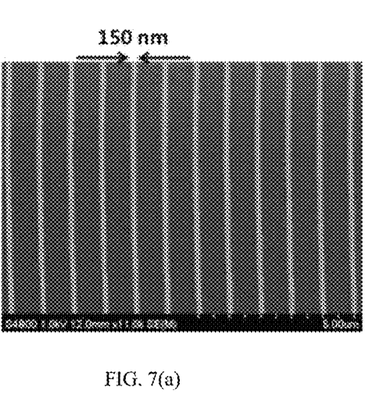
FIG. 7(a) is a front view of a grid based metamaterial.
Figure 7B:
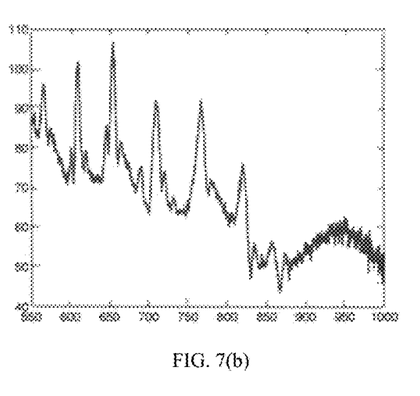
FIG. 7(b) is a transmission spectrum for the metamaterial of FIG. 7(a)

FIGS. 5 to 7 show examples of meta-atoms on flexible substrates that can be used in contact lenses. The optical properties are given for illustration purposes only.

FIG. 5(a) is an image of a metamaterial, in which the meta-atoms are defined using a "fishnet" configuration. Fishnet patterns are used for their ability to support optical resonance down to the visible range. They can be fabricated, as in this example, to be independent of light polarization. Stacking two or more membranes with a fishnet pattern, with proper alignment, can lead to the realization of negative index flexible materials, which can be used to fabricate lenses with unlimited resolution. The metamaterial of FIG. 5(a) was fabricated using gold wires of width 100 nm and with a period of 1 µm.

FIG. 5(b) shows a typical transmission spectrum, for two orthogonal polarizations, along the axes of the fishnet, and a numerical fit. It can be seen that there is good agreement between the experimental and numerical data.

FIG. 6(a) shows an example of a possible embodiment of a free-standing flexible metamaterial, with nano-antennas as meta-atoms. In this example, the polymer used is SU8 (a polymer developed by Microchem). The nano-features are realized in gold. In this case, the lattice periodicity was 1 µm in both directions, and the antenna arm lengths were 140 nm, 180 nm and 220 nm with a gap spacing of 20 to 100 nm. In nano-antennas, light is trapped an enhanced in the air gap between the gold arms. Nano-antennas resonators are typically used as optical sensor, because the resonance frequency depends strongly on the refractive of the environment.

FIG. 6(b) shows typical transmission optical spectra for different values of the geometrical parameters, as well as numerical fits for each spectra.

FIG. 7(a) shows a one-dimensional gold grating on a flexible membrane. This has a plurality of gold wires of width 100 nm and periodicity 1 µm. The reduced thickness of the membrane (4 µm in this example) induces fabry-perot resonances, which interact with the gold grating, producing narrow spectral features due to Fano-resonances. As the duty cycle is varied, it is possible to obtain both high and low transmission narrow features, with maximum and minimum value as high a 100% and 0%, respectively.

FIG. 7(b) shows a typical transmission spectrum for these meta-atoms. The possibility of plasmonic resonances with linewidth well below 1 nm, unaffected by typical detrimental losses opens the possibility for the colour response of the membrane to be controlled. This can be useful for sensing applications.

Metamaterials can be used to simplify and enhance the fabrication of multifocal contact lenses. In conventional contact lenses, multifocality is achieved via control of the thickness of the lens in different positions. With suitable meta-atoms, in 2D or 3D geometries, lens with arbitrary depths of focus can be fabricated. Alternatively, different part of the lens can be patterned with tailored meta-atoms, to ensure correct focusing for close and distant objects. The same strategy could be used to correct astigmatism, where the polarization control of metamaterials could be used to correct efficiently the vision in specific axes. This could be achieved with a single layer of meta-atoms (2D) or via a 3D stack of suitably designed meta-atoms (3D).

A suitable nanopattern can be embedded in a contact lens or realized in its surface for sensing applications. For example, plasmonic features whose response in the visible range depends on the surrounding environment could be included in the lens. For example, in one embodiment, the meta-atom could consist of nano-antennas, split ring or any other geometry with strong resonance. In other embodiments, structures supporting Fano resonance, as discussed previously, could be used to create strong indicators at very precise frequencies. For example, for a clean lens, these nanofeatures could be selected to reflect light predominantly in a specific color, e.g. green. The presence of dangerous bacteria, like *streptococcus pneumoniae*, could be revealed by the sensor via a change in the reflected frequency. In other words, contaminated lens would identified by the change in color in a small region of the lens, which could be place at the rim of the lens, to avoid interference with the visual functionality. Additionally, the plasmonic pattern could be functionalized, to specify its response to a specific contaminant. In this way, it would be possible to minimize false positive. The position of the sensor (surface or embedded in the lens) could also be used to discriminate between different contaminants, as some bacteria lies preferentially on the surface, while some others inhabits the whole lens, which is typically very permeable.

One current approach is to correct color blindness with tinted contact lenses. Tinted contact lens could be implemented by embedding on or within the lens one or more flexible metamaterials designed to selectively determine the transmitted/reflected colors. This could be used to implement colour blindness corrections functions. The complete control over the reflected/scattered colours can be also used for cosmetic reasons, without impairing vision.

Metamaterial enabled contact lenses can be used to encode information for security applications. This solution might not retain the advantage of certainty of identification, as in retina recognition applications, but would simplify greatly the readability of the information.

Contact lenses with light manipulation metamaterials could be used to track, guide and or focus light in ophthalmic surgery applications. In combination with optical sources embedded in the contact lenses, metamaterials could be used to create optoelectronic circuitry able to project in the retina virtual information, for both subject with impaired vision and healthy wearers.

A skilled person will appreciate that variations of the disclosed arrangements are possible without departing from the invention. For example, metamaterial based flexible optical devices could be also directly implanted inside the eye. Also, although only SU8 has been described as the flexible substrate, other suitable flexible materials could be used, for example, any flexible, transparent plastic or polymer, such PDMS, PMMA, Polystirene or any material used for making contact lenses, such as a suitable hydrogel, for example a hydrogel selected from any one or more of Alphafilcon A; Asmofilcon A; balafilcon A; comfilcon A; enfilcon A; etafilcon A; galyfilcon A; hilafilcon A; hilafilcon B; hioxifilcon A; hioxifilcon D; lotrafilcon B; methafilcon A; omafilcon A; phemfilcon A; polymacon; senofilcon; tetrafilcon A; vifilcon A and POLY HEMA. Any of these materials could be used alone or mixed with absorbing and/or emitting dyes. Accordingly the above description of the specific embodiment is made by way of example only and not for the purposes of limitation. It will be clear to the skilled person that minor modifications may be made without significant changes to the operation described.

The invention claimed is:

1. A contact lens or visual prosthesis comprising:
   a flexible substrate located in or on a surface of a contact lens or visual prosthesis; and
   a plurality of metamaterial optical elements formed in an array on said flexible substrate to thereby form a metamaterial element array that is flexible,
   wherein the optical elements in the array having a periodicity in the range of 1 micron to 1 nanometer and each optical element has at least one dimension in the range of 1 micron to 1 nanometer.

2. A contact lens or visual prosthesis as claimed in claim 1 wherein the separation or periodicity of the elements is in the range 50 nm to 750 nm and/or at least one dimension of each element is in the range 50 nm to 750 nm.

3. A contact lens or visual prosthesis as claimed in claim 1, wherein the optical elements are all the same.

4. A contact lens or visual prosthesis as claimed in claim 1, wherein the array or distribution comprises sub-arrays, wherein optical elements of different sub-arrays are different.

5. A contact lens or visual prosthesis as claimed in claim 1, wherein each optical element is a nano-antenna or a split ring resonant device.

6. A contact lens or visual prosthesis as claimed in claim 1, wherein each optical element is a plasmonic structure.

7. A contact lens or visual prosthesis as claimed in claim 1, wherein the optical elements are arranged or selected to alter or control the optical properties of the contact lens.

8. A contact lens or visual prosthesis as claimed in claim 7, wherein the optical elements are arranged to define or control the focal point of the lens and/or correct astigmatism and/or sense one or more defined parameters indicative of a contamination.

9. A contact lens or visual prosthesis as claimed in claim 1, wherein the optical elements are made of metal or a dielectric material.

10. A contact lens or visual prosthesis as claimed in claim 1, wherein the flexible substrate is optically transparent.

11. A contact lens or visual prosthesis as claimed in claim 1, wherein said metamaterial controls and/or manipulates light in the visible light range, 400 nm to 750 nm.

12. A contact lens or visual prosthesis as claimed in claim 1, wherein the optical elements in the array are separated from each other by a range of 1 micron to 1 nanometer.

13. A contact lens or visual prosthesis as claimed in claim 1, wherein the plurality of metamaterial optical elements are formed in the array in a fishnet pattern.

14. A contact lens or visual prosthesis as claimed in claim 1, wherein the flexible metamaterial is applied to an external surface of the contact lens or visual prosthesis.

15. A contact lens or visual prosthesis as claimed in claim 1, wherein the flexible metamaterial is applied to an internal surface of the lens and another lens material is located over the flexible metamaterial.

16. A contact lens or visual prosthesis as claimed in claim 1, wherein the metamaterial element array operates as a sensor to detect contaminates either on or in the contact lens or visual prosthesis.

17. A method for making a contact lens comprising applying a flexible metamaterial to a surface of the contact lens, wherein the flexible metamaterial comprises a flexible substrate and a plurality of metamaterial optical elements formed in an array on said flexible substrate to thereby form a metamaterial element array that is flexible, and the optical elements in the array have a periodicity in the range of 1 micron to 1 nanometer and each optical element having at least one dimension in the range of 1 micron to 1 nanometer.

18. A method as claimed in claim 17, wherein the optical elements in the array are separated from each other by a range of 1 micron to 1 nanometer.

19. A method as claimed in claim 17, wherein the plurality of metamaterial optical elements are formed in the array in a fishnet pattern.

20. A method as claimed in claim 17, wherein the flexible metamaterial is applied to an external surface of the contact lens.

21. A method as claimed in claim 17, wherein the flexible metamaterial is applied to an internal surface of the lens, and the method involves applying another lens material over the flexible metamaterial.

* * * * *